United States Patent [19]
Rivers

[11] Patent Number: 5,673,694
[45] Date of Patent: Oct. 7, 1997

[54] METHOD AND APPARATUS FOR CONTINUOUS MEASUREMENT OF CENTRAL VENOUS OXYGEN SATURATION

[75] Inventor: Emanuel Phillip Rivers, Franklin, Mich.

[73] Assignee: Henry Ford Health System, Detroit, Mich.

[21] Appl. No.: 512,462

[22] Filed: Aug. 8, 1995

[51] Int. Cl.$^6$ ..................................................... A61B 5/00
[52] U.S. Cl. ............................................. 128/634; 356/41
[58] Field of Search .................................. 128/633, 634, 128/637, 673; 356/41

[56] References Cited

U.S. PATENT DOCUMENTS

| | | | |
|---|---|---|---|
| 5,271,398 | 12/1993 | Schlain et al. | 128/634 |
| 5,284,138 | 2/1994 | Kujawski | 128/673 |
| 5,315,995 | 5/1994 | Rivers | 128/634 |
| 5,435,308 | 7/1995 | Gallup et al. | 128/634 |

OTHER PUBLICATIONS

Ander et al., "Continuous central venous oxygen saturation monitoring in the resuscitation of hemodynamically . . " *Abstracts of Posters 14th Int'l Sym. on Intensive Care and Emerg. Med.*, vol. 6, No. 2 (1995).

Ander et al., "Continuous central venous oxygen saturation monitoring as an adjunct in the treatment of cardiac arrest . . . " *Clinical Intensive Care*, 5:323–240 (1994).

Jaggi et al., "Occult cardiogenic shock in end–stage heart failure patients presenting to the Emergency Department" *Supplement to Clinical Intensive Care*, vol. 6, No. 2, p. 104 (1995).

Kowalenko et al., "Continuous central venous oxygen saturation monitoring during the resuscitation . . . " SAEM 1994 Ann. Mtg. Abstracts *Academic Emergency Medincine*, vol. 1, No. 2 A69 (1994).

Rady et al., "The responses of blood pressure, heart rate, shock index, central venous . . " *Critical Care Medicine*, A138 Jan. (1995).

Rady et al., "Continuous central venous oximety for the evaluation and treatment of acute cardiac failure in the emergency department" *International: Journal of Intensive Care*, vol. 1:64–65 Summer (1994).

Rady et al., "Continuous central venous oximetry and shock index in the emergency department —use in the evaluation of clinical shock" *American Journal of Emerg. Med.*, vol. 10, No. 6, pp. 538–541 (1992).

Rady, "The role of central venous oximetry, lactic acid concentration and shock index in the evaluation of clinical shock: a review" *Resuscitation*, 24:55–60 (1992).

Rivers et al., "The effect of the total cumulative epinerphrine dose administered during human CPR . . . " *Chest*, 106:5, pp. 1499–1507 Nov. (1994).

Rivers et al., "Continuous central venous oxygen saturation . . . " *Michigan Emergency Physician*, News & Views, vol. XIII, No. 3 May and continued in vol. XIII, No. 4 Jun./Jul. (1994).

(List continued on next page.)

*Primary Examiner*—Lee S. Cohen
*Assistant Examiner*—Eric F. Winakur
*Attorney, Agent, or Firm*—Kohn & Associates

[57] ABSTRACT

An apparatus (10) and method for measurement of oxygen saturation of venous blood for use with a central venous catheter (60) are described. The apparatus (10) includes a fiber optic bundle (12) having a distal end (14) and a proximal end (16). The fiber optic bundle (12) further includes afferent and efferent light-conducting fibers (18) for sending signals and receiving signals for generating oxygen saturation measurements. A sheath (28) is disposed about the fiber optic bundle (12) for encapsulating and protecting the fiber optic bundle (12) and exposing the distal end (14) of the fiber optic bundle (12). The apparatus (10) includes a locking device (30) for locking the fiber optic bundle (12) relative to a catheter (11) into which the fiber optic bundle (12) is inserted to fix the relative relationship between the fiber optic bundle (12) and the catheter (11) when disposed in situ during an oxygen saturation measurement procedure.

8 Claims, 2 Drawing Sheets

OTHER PUBLICATIONS

Rivers et al., "The clinical implications of continuous central venous oxygen saturation during human CPR" In *Emergency Medicine*, Chapter 1 –Acute Systems Pathophysiology, pp. 16–17.

Rivers et al., "The clinical implications of continuous central venous oxygen saturation during human CPR" *Annals of Emergency Medicine*, 21:9 Sep. (1992).

Rivers et al., "Coronary perfusion pressure, end–tidal carbon dioxide concentration and continuous central venous oxygen . . " *Supplement to Clinical Intensive Care*, vol. 3, No. 2, p. 100 (1992).

Rivers et al., "Venous hyperoxia after cardiac arrest" *Chest*, vol. 102, pp. 1787–1793, Dec. (1992).

Rivers, et al., "Coronary perfusion pressure, end–tidal carbon dioxide concentration and continuous central venous oxygen . . " Abstracts of Papers, Presentations Cardiopulmonary Resuscitation S85.

METHOD AND APPARATUS FOR CONTINUOUS MEASUREMENT OF CENTRAL VENOUS OXYGEN SATURATION

TECHNICAL FIELD

This invention relates to a method and apparatus for measuring central venous oxygen saturation and treatment during human cardiopulmonary resuscitation (cardiac arrest) and clinical shock, and more particularly to an apparatus and method for measuring central venous oxygen saturation using a standard central venous catheter.

BACKGROUND OF THE INVENTION

Cardiac arrest and shock are some of the most dynamic pathophysiological events in clinical medicine. An immediate cascade of pathologic processes is triggered in response to a decrease in oxygen delivery. Since oxygen is not stored in sufficient quantities in the body, inadequate oxygen transport to the cells for even very brief periods of time can result in organ failure and death.

Traditional medical intervention attempts to provide oxygen delivery and thereby attenuate this cascade. Rapid and substantial improvement in oxygen delivery is required to decrease the morbidity and mortality of ischemic organ injury. Current monitoring techniques include continuous electrocardiographic monitoring and measurement of blood pressure. Both of these techniques provide little information regarding hemodynamic status and/or oxygen delivery to the brain or body (tissues).

Mixed venous oxygen saturation ($SvO_2$) is the amount of oxygen in blood taken from a vessel coming from the right side of the heart going into the lungs. This reflects the amount of oxygen being delivered to the tissues during cardiac arrest and shock. Selective venous hypoxemia or low oxygen content, when compared to arterial blood, are characteristically seen during cardiac arrest and shock.

When oxygen delivery to the tissues is low, the $SvO_2$ is low. When oxygen delivery to the tissues is high, the $SvO_2$ is normal or high. This provides the physiological basis for using $SvO_2$ as an indicator of response to therapy during treating a patient in cardiac arrest or shock. Intermittent $SvO_2$ measurement can be predictive of outcome in cardiac patients and hemodynamically unstable trauma patients and medical patients.

Ideally, $SvO_2$ should be drawn from a pulmonary artery catheter which is approximately 65 centimeters long and is placed into a vein that assesses the right side of the heart and then into the pulmonary artery. However, placement of a pulmonary artery catheter is extremely difficult and can be impractical during cardiac arrest and severe shock due to low blood pressure.

The central venous system is located much closer to the skin and can be more easily accessed during shock and cardiac arrest. Thus, a number of studies have supported the substitution of central venous (right atrial or superior vena cava) oxygen saturation ($ScvO_2$) for pulmonary artery blood oxygen saturation ($SvO_2$) during spontaneous circulation, circulatory failure, and closed chest CPR. The central venous blood can be obtained much more easily than blood from the pulmonary artery under conditions of shock and cardiac arrest. Thus, it is more feasible to use the central venous system as it provides similar information.

As stated above, current monitoring techniques used in treating patients in cardiac arrest and shock rely on heart rate and measurement of blood pressure. Both of these techniques provial little information regarding hemodynamic status and/or oxygen delivery to the brain or body (tissues). In fact, research reveals that patients in cardiac arrest and shock whose treatment is guided by heart rate and blood pressure may still be still in shock even after blood pressure and heart rate have been corrected to normal levels.

Clinical monitoring techniques used as prognostic and therapeutic indicators during cardiac arrest include the coronary perfusion pressure (CPP), aortic to right atrial relaxation phase pressure gradients, and end-tidal carbon dioxide concentration ($ETCO_2$). The importance of CPP as a prognostic indicator of return of spontaneous circulation (ROSC) during animal and human cardiopulmonary resuscitation (CPR) is well established. CPP is the "gold" standard for measuring hemodynamic response to therapy during CPR. Calculation of CPP requires placement of both an aortic artery catheter and a central venous catheter which may limit its applicability.

$ETCO_2$ has been studied in animals and humans and has been proposed as a prognostic and therapeutic guide during CPR. Although $ETCO_2$ has the advantage of being noninvasive, it is influenced by multiple variables (i.e. aspiration, pre-existing pulmonary disease) which may limit its true reflection of blood flow and CPP in the cardiac arrest setting.

In a study comparing CPP and ETCO2 to $ScvO_2$ during the treatment of cardiac arrest, $ScvO_2$ was shown to be a better indicator of survival and response to therapy. [Rivers et al., 1992b; Rivers et al., 1992a].

Continuous monitoring of $ScvO_2$ during the treatment of a critically ill patient in shock has also been shown to provide both therapeutic and prognostic information for the treatment and management of patients in these conditions. [Rivers et al., 1992a]. Patients presenting in shock (low blood pressure and elevated heart rate) to the Emergency Department were treated to establish a normal blood pressure and heart rate. More than 50% of these patients continued to remain in shock as determined by decreased $ScvO_2$. These patients required additional therapy that would have not been given if only blood pressure and heart rate were relied upon for determining treatment. For a general review of $ScvO_2$ during treatment of a patient in shock, see Ander et al., "Continuous Central Venous Oxygen Saturation Monitoring as an Adjunct in the Treatment of Cardiac Arrest and Shock: Principles and Practice" *Clinical Intensive Care* 5:232–240, 1994.

Fiber optic technology has previously been utilized in measuring $ScvO_2$. U.S. Pat. No. 5,315,995 to Rivers ('995), issued May 31, 1994, describes a fiber optic catheter and its efficacy for continuous measurement of central venous oxygen saturation. The catheter includes a catheter body having a fiber optic bundle disposed therein. In operation, this catheter is inserted into the subclavian vein or internal jugular vein with the aid of a catheter introducer or guide wire.

When placing the catheter using a guide wire, the guide wire is placed into a vein. The catheter is then threaded over the guide wire and guided into the vein. When the catheter is correctly positioned within the vein, it has to be secured to the skin with stitches or sutures to avoid movement. Movement will decrease the quality of the signal or dislodge the catheter from the patient.

When the catheter goes through the skin over the guide wire into the vein, the tip of the catheter, where the fiber optic bundle exits, can be damaged by the surrounding tissue as it penetrates. This damage can cause alteration in the fiber optic bundle which could lead to erroneous measurement of $ScvO_2$.

The insertion of this catheter can also be performed through an introducer. An introducer is a small plastic tube that is placed through the skin into the vein and serves as a tunnel or passageway. The catheter is then guided through the introducer into the vein. Once the catheter is correctly positioned within the vein, it is also sutured or stitched to the skin to prevent movement of the catheter which could cause decreased signal quality and to avoid dislodging of the catheter from the patient. Whether the catheter is placed over a guide wire or inserted through an introducer, both techniques require an x-ray of the patient to determine if placement inside the patient is correct.

Disadvantages of using either the guide wire and the introducer were discovered through research in more than 350 patients. If the catheter is placed using the guide wire or the introducer and is secured, it must be replaced if it is in the incorrect position within the patient. This requires the expense of replacing another catheter, removing and then replacing the stitches, and repeating the x-ray to determine correct placement. When a patient is acutely ill, replacing the existing catheter requires a significant amount of time that could be detrimental to the patient. Furthermore, repeating the suturing and replacing the catheter into the vein is painful to the patient and further poses a greater risk of infection, collapsed lung, laceration or tear of a blood vessel in the chest and the potential of air bubbles entering the patient's vein and going into the heart or brain. These complications can cause serious illness and even death. Additionally, when another catheter is used, an additional x-ray is required. This adds additional health care costs and exposes the patient and health care personnel to more radiation.

Currently, in order to use a fiber optic bundle to obtain oxygen saturation measurement when a standard central venous catheter has been previously inserted into a patient, it is necessary to remove the standard catheter and insert a new catheter such as the '995 catheter/fiber optic bundle combination. This is costly, may require another x-ray to confirm proper positioning, and introduces the potential for infection. Furthermore, placing another catheter into the patient can cause complications such as a collapsed lung or severe bleeding.

Therefore, it would be desirable to have an apparatus which provides for the measurement of oxygen saturation which is adapted for use with any central venous catheter, thereby eliminating the drawbacks of prior measurement devices.

The present invention utilizes an adaptor which allows a fiber optic bundle to be placed into any standard central venous catheter and, thereby provides a substantial improvement over known prior art devices.

SUMMARY OF THE INVENTION AND ADVANTAGES

In accordance with the present invention, there is provided an oxygen saturation measurement apparatus for use with a central venous catheter including a fiber optic bundle having a distal end and a proximal end. The fiber optic bundle includes afferent and efferent light-conducting fibers for sending signals and receiving signals for generating oxygen saturation measurements. A sheath disposed about the fiber optic bundle encapsulates and protects the fiber optic bundle and exposes the distal end of the fiber optic bundle. A locking device is provided for locking the fiber optic bundle relative to a catheter into which the fiber optic bundle is inserted to fix the relative relationship between the fiber optic bundle and the catheter when disposed in situ during an oxygen saturation measurement procedure.

The present invention further provides a method for measurement of oxygen saturation of venous blood which includes the steps of inserting a catheter having both distal and proximal ends into a central venous blood vessel. Connecting a fitting to the centra venous catheter which allows for both insertion of a fiber optic bundle and fixing of the fiber optic bundle relative to a catheter into which the fiber optic bundle is inserted. The method further includes the steps of inserting the fiber optic bundle, including afferent and efferent light-conducting fibers for sending signals and receiving signals for generating oxygen saturation measurements, into the catheter and locking the position of the fiber optic bundle relative to the catheter to fix the relative relationship between the fiber optic bundle and the catheter when disposed in situ during an oxygen saturation measurement procedure and continuously monitoring the oxygen saturation of the venous blood.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1:
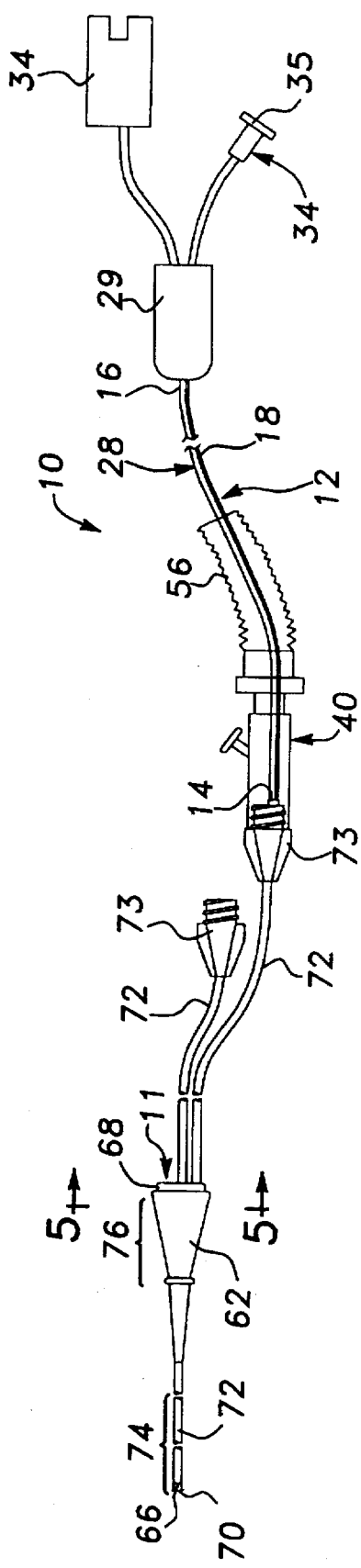
FIG. 1 is a schematic diagram illustrating the apparatus of the present invention.

Referring to FIG. 1, an apparatus generally indicated at 10 is shown for use with a central venous catheter 11 for measuring central venous oxygen saturation ($ScvO_2$). The apparatus 10 comprises a fiber optic bundle generally shown at 12 having a distal end 14 and a proximal end 16. The fiber optic bundle 12 includes afferent and efferent light-conducting fibers 18 for sending signals and receiving signals for generating oxygen saturation measurements. A sheath 28 is disposed about the fiber optic bundle 12 and encapsulates and protects the fiber optic bundle 12 and exposes the distal end 14 of the fiber optic bundle 12. A locking device 40 for locking the fiber optic bundle 12 relative to a catheter 11 into which the fiber optic bundle 12 is inserted to fix the relative relationship between the fiber optic bundle 12 and the catheter 11 when disposed in situ, i.e., in a blood vessel, during an oxygen saturation measurement procedure.

Figure 2:
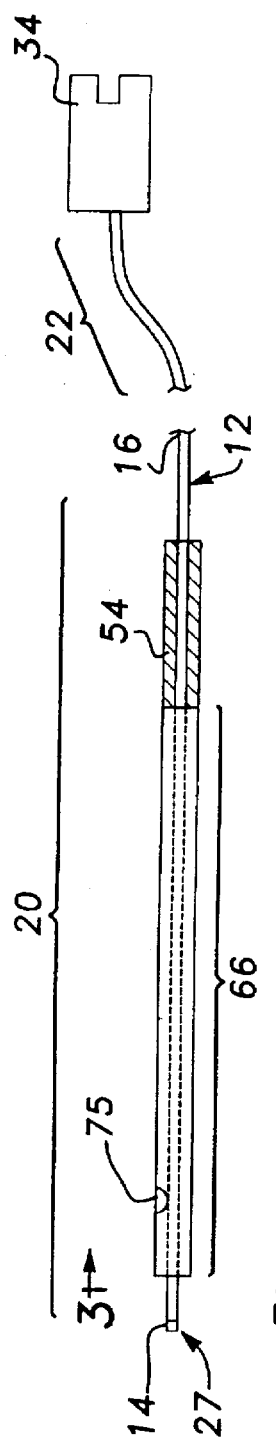
FIG. 2 is a cross-sectional side view of the invention of the present invention showing the apparatus of the present invention inserted into a catheter.

Referring to FIG. 2, the fiber optic bundle 12 includes a distal portion 20 and a proximal portion 22. The distal portion 20 includes the region of the fiber optic bundle 12 that is inserted into the standard venous catheter 11 such as an Product No. CS-17702, Arrow International, Inc., Reading, Pa. The proximal portion 22 of the fiber optic bundle 12 includes the region that transmits light signals to and from a light generator/detector where the light is analyzed yielding a measurement of venous oxygen saturation. The fibers 18 spectrophotometrically reflect light transmitted therethrough. The light is transmitted from a light source through the fiber optic bundle 12 into the blood. Light reflected off of red blood cells is picked up and transmitted along the fiber optic bundle 12 back to a photo-detector where the signal is analyzed. The amount of light reflected at different wavelengths varies depending on the concentration of oxyhemoglobin and hemoglobin present in the blood. The relative ratios of oxyhemoglobin and hemoglobin is used to calculate and determine the $ScvO_2$.

Figure 3:
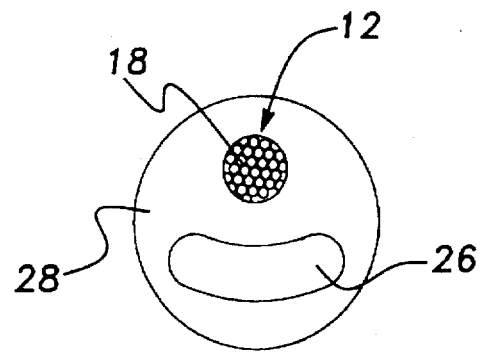
FIG. 3 is a sectional view of the apparatus of the present invention taken along line 3—3 in FIG. 2.

The fiber optic bundle 12 is disposed in a sheath or cover 28 which both encapsulates and protects the fiber optic bundle 12 as shown in FIG. 3. The sheath 28 can also define a lumen 26 disposed therein extending longitudinally the entire length of the distal portion 20 of the fiber optic bundle 12. A preferred embodiment of the present invention provides a sheath 28 which extends along the distal portion 20 of the fiber optic bundle 12 from the distal end 14 of the bundle 12 to an optional junction 29. At the distal end 14 of the distal portion of the fiber optic bundle 12 as shown in FIG. 2, the sheath 28 is absent, thereby allowing for the fiber optic bundle 12 to be in direct contact with the blood for taking oxygen saturation measurements and also to expose the distal or open end 27 of the lumen 26 thereby facilitating sampling, pressure measurement, or fluid/pharmaceutical administration.

The sheath 12 includes markings or delineations which are located at preselected distances from the distal end 14 of the bundle 12 which provide a visual indication of fiber optic bundle insertion depth. This indication of fiber optic bundle insertion depth aids the practitioner in proper placement of the bundle within a patient.

As shown in FIG. 1, the apparatus 10 includes the optional junction 29. In this embodiment, the sheath 28 defines a single lumen 26 which extends from the junction 29 the entire length of the distal portion 20 of the fiber optic bundle 12. The junction 29 permits access to the lumen(s) 26 through a port 34 and also is the location where the distal portion 20 of the fiber optic bundle 12 becomes separated from the lumen 26. The proximal portion 22 of the fiber optic bundle 12 extends to a connector body 36 which is then connected to the light generator/detector (not shown), such as an Oximetry 3 Oximetry System, Abbott Critical Care Systems, Mountainview, Calif., which can be computer controlled. The porn 34 extending from the junction 29 can include a tube having a connector 35 attached thereto.

The outer diameter of the sheath 28 containing the fiber optic bundle 12 should be less than the inner diameter of the lumen or port of the catheter 11 into which the fiber optic bundle 12 is inserted. Additionally, the sheath 28 is preferably constructed of a self-lubricating material to facilitate insertion and removal of the 28 encapsulated fiber optic bundle 12 from a catheter 11. Such a self-lubricating material could include silicone.

The locking device 40 is adapted to both connect the apparatus 10 of the present invention to a standard venous catheter 11 and to fix or retain the distal portion 20 of the fiber optic bundle 12 with respect to the catheter 11 when the fiber optic bundle 12 is inserted into the catheter 11. The locking device 40 enables more accurate oxygen saturation measurement to be taken since it prevents movement of the fiber optic bundle 12 once it has be properly positioned in the blood vessel. Additionally, the locking device 40 does not require stitching of the fiber optic bundle 12 to the patient's skin to prevent movement of the fiber optic bundle 12, thereby eliminating a potential source of infection. Therefore, if the necessity for removing or repositioning the fiber optic bundle 12 arises, it would only require loosening of the locking device 40 to reposition or reinsert the fiber optic bundle 12, not requiring removing stitches, insertion of a new catheter, and reinserting new stitches as is currently the procedure.

Figure 4:
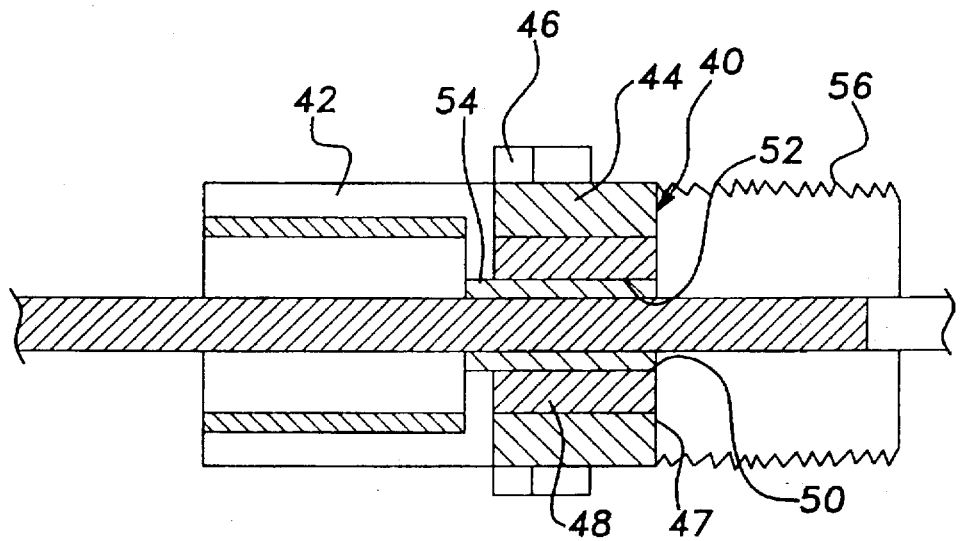
FIG. 4 is a sectional view of the locking device of the present invention.

Referring to FIG. 4, the locking device 40 includes a connector 42 operatively connected in fluid communication to the locking device 40 for attaching the locking device 40 to the catheter 11. The connector 42 can be any suitable connector, such as a quick-release or Luer-type connector, or other screw down-type connector known to those skilled in the art.

As shown in FIG. 4, the locking device 40 can include a threaded male insert 44 in mating engagement with a female locking member 46. The locking member 46 includes a flange 47 having a resilient insert 48 abutting thereto. The flange 47 and the insert each have an opening 50,52, respectively, to allow for the insertion and support of the distal portion 22 of the fiber optic bundle 12. The resilient insert 48 can be constructed of any suitable material which, when the locking member 46 is matingly engaged with the male insert 44, compresses the resilient insert 48 causing its opening to become smaller 52.

When the distal portion 20 of the fiber optic bundle 12 is present within the opening 52 of the resilient insert 48 and the locking member 46 is then engaged with the male insert 44, the insert 48 compresses and engages the sheath 28 over the fiber optic bundle 12 thereby preventing movement of the distal portion 20 of the fiber optic bundle 12 within the locking device 40 and within the catheter 11.

The region of the distal portion 20 of the fiber optic bundle 12 to which the locking device 40 engages can include a reinforcement 54 disposed about the sheath 28 or integrally formed with the sheath 28 to prevent damage to the sheath 28 and fiber optic bundle 12 caused by the compression forces of the locking device 40. This reinforcement 54 can include a concentric layer of a harder or higher durometer plastic material such as silicone, PVC, polypropylene, metal or metal alloy, etc.

The locking device 40 can further include a protective sleeve 56 fixedly attached to the locking member 46 for protecting and maintaining sterility of the sheath 28. The protective sleeve 56 allows the sheath 28 encapsulated fiber optic bundle 12 to pass therethrough. The protective sleeve 52 can be formed of any suitable material, such as cellophane or polyvinylidene chloride which allows the sleeve 52 to contract or expand in an "accordion-like" fashion when the fiber optic bundle 12 is inserted or removed to constantly cover and maintain sterile the distal portion 20 of the fiber optic bundle 12 and sheath 28.

Figure 5:
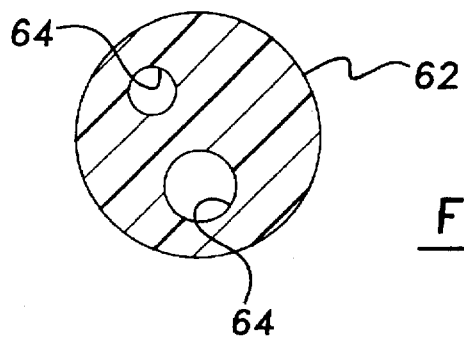
FIG. 5 is a sectional view of the catheter taken along line 5—5 of FIG. 1.

Referring to FIGS. 1 and 5, the catheter 11 used in conjunction with the present invention includes a body 62 forming at least one and preferably more than one lumen 64 therein. The catheter body 62 has a distal 66 and a proximal 68 end. The lumen(s) 64 extend(s) longitudinally within the catheter body 62 from a distal opening(s) 70 to a proximal port(s) 72.

The catheter sheath 28 can also include markings or delineations which provide a practitioner with information about the depth of the catheter insertion into a patient. The information provided to the practitioner by these markings aids in the proper insertion and placement of the catheter 11 into the patient.

The catheter body 62 includes a blood vessel insertion portion 74 and a lumen junction 76. The blood vessel insertion portion 74 is adapted to be inserted into a blood vessel, such as the subclavian vein, supraclavicular vein, and internal jugular vein, and preferably has a length of at least 20 cm. The blood vessel insertion portion 74 should be capable of flexing to facilitate insertion of the catheter 11 into the blood vessel but should also have sufficient rigidity such that it will not be unduly flexed under the force of turbulent blood flow.

The blood vessel insertion portion 74 also includes an opening 75 located at the distal end 66 of the catheter body 62. This opening 75 permits the distal end 20 of the fiber optic bundle 12 to exit or protrude beyond the blood vessel insertion portion 74 of the catheter body 62.

The blood vessel insertion portion 74 of the catheter body 62 can be constructed of any suitable biologically compatible material, such as polyurethane, known to those skilled in the art.

The lumen junction 76 is the portion of the catheter body 62 at which point each lumen 64 included in the blood vessel insertion portion 74 of the catheter body 62 is translated into separate port(s) or tubes 72 such as for a sampling port or an insertion port for the fiber optic bundle 12. For example, as shown in FIG. 1, a two lumen catheter 11 has two ports which proximally extend from the lumen junction 76 each port permitting access to each individual lumen 64 for inserting or withdrawing fluids therethrough and/or inserting or withdrawing the fiber optic bundle 12.

Each port 72 has a connector 73 which allows the port 72 to be connected to other devices or fittings such as a hypodermic needle or intravenous fluid injection port or to a fitting which allows connection and insertion of a fiber optic bundle 12. The connector 73 can be any suitable type connector known in the art, such as a quick-release or Luer-type connector or a screw down-type connector.

In operation, a standard central venous catheter 11 having at least one lumen is percutaneously inserted, properly positioned and secured into the central venous system through the subclavian vein. The connector 42 of the locking device 40 would then be connected to a fitting 73 on the catheter 11 to allow for the insertion of the fiber optic bundle 12 within the catheter 11. The fiber optic bundle 12 would then be inserted through the locking device into the catheter 11 and positioned such that the distal tip of the fiber optic bundle 12 extends beyond the distal opening of the catheter 11 preferably into the right atrium. The markings or delineations on the catheter sheath 28 would provide information about the depth of the catheter insertion within the patient. The location of the fiber optic bundle 12 is then fixed relative to the catheter 11 by applying the locking member to the sheath covering the fiber optic bundle 12.

Prior to insertion of the fiber optic bundle 12 in situ (in a blood vessel), the apparatus 10 is electronically calibrated. Then, using a sample of venous blood taken from the patient, the fiber optic bundle 12 can be re-calibrated in situ, if necessary.

Following catheterization and fiber optic bundle 12 insertion and fixation, continuous measurements and monitoring of the central venous oxygen saturation are obtained.

Should it be necessary to remove the fiber optic bundle 12 from the catheter 11, the fiber optic bundle 12 can be removed and the catheter 11 used for other purposes. Utilizing the apparatus 10 of the present invention, a fiber optic bundle 12 can be reinserted into the original catheter 11 thereby eliminating the expense of replacing the catheter 11. This would also reduce the delay in time, associated expense, and patient discomfort which would have been caused by having to replace the catheter 11 and take an x-ray to ascertain proper placement of the catheter 11.

Throughout this application various publications are referenced by citation or number. Full citations for the publication are listed below. The disclosure of these publications in their entireties are hereby incorporated by reference into this application in order to more fully describe the state of the art to which this invention pertains.

The invention has been described in an illustrative manner, and it is to be understood the terminology used is intended to be in the nature of description rather than of limitation.

Obviously, many modifications and variations of the present invention are possible in light of the above teachings. Therefore, it is to be understood that within the scope of the appended claims, reference numerals are merely for convenience and are not to be in any way limiting, the invention may be practiced otherwise than as specifically described.

References

Anders et al., *Clinical Intensive Care*, 5:232–240, (1994).

Rivers et al., "The Clinical Implications of Continuous Central Venous Oxygen Saturation Monitoring During Human Cardiopulmonary Arrest" *Annals of Emergency Medicine*, 21:1094–1101, (1992a).

Rivers et al., "Coronary Perfusion Pressure, End-Tidal Carbon Dioxide Concentration And Continuous Central Venous Oxygen Saturation Monitoring As A Predicator Of Outcome During Human CPR" *Clinical Intensive Care* 3(2):100, (1992b).

I claim:

1. An oxygen saturation measurement apparatus for use with a central venous catheter, said apparatus comprising:

a fiber optic bundle having a distal end and a proximal end said fiber optic bundle including afferent and efferent light-conducting fiber means for sending signals and fox receiving signals for generating venous oxygen saturation measurements related to lung function heart function and blood content simultaneously;

sheath means disposed about said fiber optic bundle for encapsulating and protecting said fiber optic bundle; wherein said distal end of said fiber optic bundle remains exposed and locking means for locking said fiber optic bundle relative to a catheter into which said fiber optic bundle is inserted to fix the relative relationship between said fiber optic bundle and the catheter when disposed in situ during an oxygen saturation measurement procedure.

2. An apparatus as set forth in claim 1, wherein said locking means includes connector means connected to said locking means for attaching said locking means to the catheter.

3. An apparatus as set forth in claim 1, wherein said sheath means includes at least one lumen extending to a distal port on said sheath means to allow for pressure measurement and sampling.

4. An apparatus as set forth in claim 1, wherein said sheath means further includes reinforcing means disposed about said sheath means for preventing damage to said sheath means caused by said locking means.

5. An oxygen saturation measurement apparatus for use with a central venous catheter, said apparatus comprising:

a fiber optic bundle having a distal end and a proximal end, said fiber optic bundle including afferent and efferent light-conducting fiber means for sending signals and for receiving signals for generating venous oxygen saturation measurements related to lung function heart function and blood content simultaneously;

sheath means disposed about said fiber optic bundle for encapsulating and protecting said fiber optic bundle, wherein said distal end of said fiber optic bundle, remains exposed;

locking means for locking said fiber optic bundle relative to a catheter into which said fiber optic bundle is inserted to fix the relative relationship between said fiber optic bundle and the catheter when disposed in situ during an oxygen saturation measurement procedure and, said locking means further including sleeve means operatively attached to said locking means for protecting and maintaining sterility of said sheath means disposed about said fiber optic bundle.

6. A method for measurement of oxygen saturation of venous blood, said method including the steps of:

inserting a catheter into a central venous blood vessel;

connecting a fitting to the catheter which allows for both insertion of a fiber optic bundle and fixing of the fiber optic bundle relative to the catheter into which the fiber optic bundle is inserted;

inserting the fiber optic bundle into the catheter;

locking the position of the fiber optic bundle relative to the catheter to fix the relative relationship between the fiber optic bundle and the catheter when disposed in situ during an oxygen saturation measurement procedure; and continuously monitoring the oxygen saturation of the venous blood related to lung function, heart function and blood content simultaneously.

7. A method as set forth in claim 6, wherein said locking step further includes the step of adjusting an mount of the fiber optic bundle which extends beyond a distal end of the catheter.

8. A method for measurement of oxygen saturation of venous blood said method including the steps of:

inserting a catheter into a central venous blood vessel;

connecting a fitting to the catheter which allows for both insertion of a fiber optic bundle and fixing of the fiber optic bundle relative to the catheter into which the fiber optic bundle is inserted;

inserting the fiber optic bundle into the catheter:

locking the position of the fiber optic bundle relative to the catheter to fix the relative relationship between the fiber optic bundle and the catheter when disposed in situ during an oxygen saturation measurement procedure;

continuously monitoring the oxygen saturation of the venous blood related to lung function heart function and blood content simultaneously, and reinserting said fiber optic bundle into the originally placed catheter following previous removal of said fiber optic bundle from the catheter.

* * * * *